United States Patent
Saya et al.

(10) Patent No.: US 11,400,076 B2
(45) Date of Patent: Aug. 2, 2022

(54) CANCER STEM CELL INHIBITOR

(71) Applicants: KEIO UNIVERSITY, Minato-ku (JP); POLA PHARMA INC., Shinagawa-ku (JP)

(72) Inventors: Hideyuki Saya, Shinjuku-ku (JP); Oltea Sampetrean, Shinjuku-ku (JP); Naoyoshi Koike, Shinjuku-ku (JP); Nobuo Kubota, Shinagawa-ku (JP)

(73) Assignees: KEIO UNIVERSITY, Minato-ku (JP); Sun Pharma Japan Limited, Tokyo (JP)

(*) Notice: Subject to any disclaimer, the term of this patent is extended or adjusted under 35 U.S.C. 154(b) by 42 days.

(21) Appl. No.: 16/753,209

(22) PCT Filed: Oct. 2, 2018

(86) PCT No.: PCT/JP2018/036792
§ 371 (c)(1),
(2) Date: Apr. 2, 2020

(87) PCT Pub. No.: WO2019/069891
PCT Pub. Date: Apr. 11, 2019

(65) Prior Publication Data
US 2020/0316027 A1     Oct. 8, 2020

Related U.S. Application Data (60) Provisional application No. 62/587,195, filed on Nov. 16, 2017, provisional application No. 62/566,695, filed on Oct. 2, 2017.

(51) Int. Cl.
*A61K 31/4168*     (2006.01)
*A61K 45/06*     (2006.01)

(52) U.S. Cl.
CPC .......... *A61K 31/4168* (2013.01); *A61K 45/06* (2013.01)

(58) Field of Classification Search
CPC ................................................ A61K 31/4168
See application file for complete search history.

(56) References Cited

U.S. PATENT DOCUMENTS 8,258,165 B2* 9/2012 Murakami ........... A61K 9/0019
514/398
9,814,707 B2* 11/2017 Saya ..................... A61K 31/655
2017/0105984 A1   4/2017 Saya et al.

FOREIGN PATENT DOCUMENTS

| JP | 8-291064 A | 11/1996 |
| JP | 9-77667 A | 3/1997 |
| JP | 2005-27515 A | 2/2005 |
| JP | 2007-302610 A | 11/2007 |
| JP | 2007-326814 A | 12/2007 |
| JP | 2017-31059 A | 2/2017 |

OTHER PUBLICATIONS

International Search Report dated Dec. 4, 2018 in PCT/JP2018/036792 filed on Oct. 2, 2018, 2 pages.
Bao, S. et al., "Glioma stem cells promote radioresistance by preferential activation of the DNA damage response," Nature, vol. 444, doi:10.1038/nature05236, Dec. 2006, pp. 756-760.
Heddleston, J. M. et al., "The hypoxic microenvironment maintains glioblastoma stem cells and promotes reprogramming towards a cancer stem cell phenotype," Cell Cycle, vol. 8, Issue 20, Oct. 2009, pp. 3274-3284, 12 total pages.
Lathia, J. D. et al., "Direct In Vivo Evidence for Tumor Propagation by Glioblastoma Cancer Stem Cells," PLoS One, vol. 6, Issue 9, e24807, Sep. 2011, pp. 1-9.
Matsuoka, H. et al., "In vivo efficacy and pharmacokinetics of a new hypoxic cell radiosensitizer doranidazole in SUIT-2 human pancreatic cancer xenografted in mouse pancreas," Oncology Reports, vol. 7, 2000, pp. 23-26.
Yoon, C. et al., "Multimodal targeting of tumor vasculature and cancer stem-like cells in sarcomas with VEGF-A inhibition, HIF-1α inhibition, and hypoxia-activated chemotherapy," Oncotarget, vol. 7, No. 28, Jun. 2016, pp. 42844-42858.
Li, Q. et al., "Hypoxia-activated cytotoxicity of benznidazole against clonogenic tumor cells," Cancer Biology & Therapy, vol. 17, No. 12, 2016, pp. 1266-1273.
Benito, J. et al., "Hypoxia-Activated Prodrug TH-302 Targets Hypoxic Bone Marrow Niches in Preclinical Leukemia Models," Clinical Cancer Research, vol. 22, No. 7, 2016, pp. 1687-1698, 13 total pages.
Extended European Search Repot dated Jun. 2, 2021 for European Patent Application No. 18864483.5, 12 pages.
Terry J. Miller, et al., "CI-1010 induced opening of the mitochondrial permeability transition pore precedes oxidative stress and apoptosis in SY5Y neuroblastoma cells," Brain Research, vol. 963, XP055805716, 2003, pp. 43-56.
S. B. Howell, et al., "Interaction between Misonidazole and Chemotherapeutic Agents against Human Marrow and Tumor Stem Cells under Oxic and Hypoxic Conditions," Stem Cells, vol. 1, No. 4-5, XP055805387, Jan. 1, 1981, p. 310.
David I Edwards, "Mechanisms of selective toxicity of metronidazole and other nitroimidazole drugs," Br J Vener Dis., vol. 56, XP055805002, 1980, pp. 285-290.
Jerry J. Gipp, et al., "DNA damage induced in HT-29 colon cancer cells by exposure to 1-methyl-2-nitrosoimidazole, a reductive metabolite of 1-methyl-2-nitroimidazole," Biochemical Pharmacology, vol. 42, Supplement, XP023731394, 1991, pp. S127-S133.
Dietmar W. Siemann, et al., "Combinations of cyclophosphamide and misonidazole in the KHT sarcoma," International Journal of Radiation: Oncology Biology Physics, vol. 8, No. 3-4, XP026841652, 1982, pp. 647-650.

(Continued)

*Primary Examiner* — Golam M Shameem
(74) *Attorney, Agent, or Firm* — Oblon, McClelland, Maier & Neustadt, L.L.P.

(57) ABSTRACT

The object of the present invention is to provide a novel pharmaceutical for suppressing cancer stem cells. In the present invention, a mitochondria inhibitor comprising a 2-nitroimidazole derivative is applied to the cancer stem cell as an active ingredient.

6 Claims, 10 Drawing Sheets

(56) References Cited

OTHER PUBLICATIONS

Katsuyuki Karasawa, et al., "Efficacy of novel hypoxic cell sensitiser doranidazole in the treatment of locally advanced pancreatic cancer: Long-term results of a placebo-controlled randomised study," Radiotherapy and Oncology, vol. 87, XP022731790, 2008, pp. 326-330.

"Abstracts the Metastasis Research Society—American Association for Cancer Research Conference on Metastasis", Clinical & Experimental Metastasis, vol. 26, XP019747312, 2009, pp. 849-934.

R. A. Smith, "Mitochondrial alterations produced by misonidazole: a study using *Amoeba proteus* as a single-cell model", British Journal of Cancer, vol. 41, XP055807140, 1980, pp. 305-308.

\* cited by examiner

CANCER STEM CELL INHIBITOR

FIELD OF THE INVENTION

The present invention relates to pharmaceuticals for suppressing cancer stem cells, and more particularly, to pharmaceuticals for suppressing cancer stem cells based on inhibition of mitochondria.

BACKGROUND OF THE INVENTION

Cancer stem cells are highly undifferentiated malignant cells which also act as sources of cancer cells, while self-replicating, and known as having high antioxidant capacity (i.e. cells having developed antioxidative defense mechanism). Normal cancer cells are killed by, for example, chemotherapy, radiation, and molecular-targeted drugs, whereas cancer stem cells cannot be attacked by these therapies, therefore, these cells make complete cure of cancer more difficult (for example, see, Patent Literature 1). Furthermore, cancer stem cells are undifferentiated and thus tend to become metastatic cancer. In other words, the cancer stem cells are known to account for a large proportion of cancers generated due to metastasis. For example, melanoma, glioma, and sarcoma are known as cancer having relatively more cancer stem cells. Furthermore, substantially no therapeutic agents for cancer stem cells have been developed so far, and this is the largest bottleneck in cancer therapy.

Generation of cancer stem cells is basically classified into two types, and one is a type in which normal stem cells themselves undergo malignant transformation. This type of cancer stem cell is often observed in, for example, pediatric cancer and blood cancer. This type of cancer maintains most of properties of general stem cells, and because it grows slowly, its interaction with anticancer agents becomes poor. The other is a type in which cells differentiated to a certain degree are transformed into cancer stem cells due to existence of long-term inflammation. Such a type of cell is observed in general cancers which develop after late middle age. Although this type of cell grows relatively rapidly, the cell shows resistant to oxidative stress and anticancer agents. In summary, in cancer therapy, the presence of cancer stem cells makes these therapies difficult. The facts that cancer stem cells have therapy resistance, particularly, therapy resistance to radiation; that cancer stem cells are also present under normoxic condition; and that cancer stem cells have therapy resistance even under normoxic condition, make the therapy for such cells different from general cancer therapy. Furthermore, despite the metabolism is usually suppressed in hypoxic cells, in the case of cancer stem cells, the metabolism is not significantly suppressed, the metabolism in mitochondria is carried out, and also the capacity of processing generated reactive oxygen species is enhanced. This is also responsible for difficulty in therapy (for example, see Non-Patent Literatures 1 and 2). In another words, a means for suppressing growth of cancer stem cells for therapy has been required.

Meanwhile, a 2-nitroimidazole derivative represented by doranidazole, misonidazole and etanidazole, of which the structure is shown below, is known for its effect as a hypoxic cell radiosensitizer. However, the 2-nitroimidazole derivative hardly exhibits toxicity to normal differentiated cancer cells under hypoxic condition and normoxic condition. It is known that the 2-nitroimidazole derivative attacks hydroxide of thymidine in DNA, induces apoptosis of cancer cells, and thus exhibits a cancer therapy effect only when radiation is administered under hypoxic condition (for example, see Patent Literatures 2 and 3). This effect is similarly exhibited even in a case where radiotherapy is changed to hyperthermia (for example, see Patent Literatures 4 and 5). These studies are all conducted in the presence of differentiation-inducing factors. The effect of 2-nitroimidazole derivative in undifferentiated cancer cells has not been studied so far.

Furthermore, there is a report that the 2-nitroimidazole derivative exhibits an anticancer effect for pancreatic cancer under hypoxic condition (for example, see Patent Literature 6). However, the degree of the suppression effect is very low, and it is therefore difficult to say that these derivatives definitely have an effect of killing cancer cells (for example, see Non-Patent Literature 4). Such studies are all conducted in the presence of differentiation-inducing factors, and thus the effect thereof is assumed to be an effect on differentiated cancer cells. Therefore, there is no relationship between the effect and undifferentiated cancer stem cells.

In cancer stem cells, respiration and metabolism in mitochondria play an important role, and processing of reactive oxidative species (ROS) generated in this process is an important issue for surviving. However, the relationship between the 2-nitroimidazole derivative and ROS has not been studied at all, and there is no information thereof.

To summarize, it can be said that the effects on cancer stem cells of the 2-nitroimidazole derivative, typically doranidazole, have not been known at all.

According to above, although a practical means for suppressing cancer stem cells has been required, such a means has not been found at present.

CITATION LIST

Patent Literature

Patent Literature 1: JP 2017-31059 A
Patent Literature 2: JP 09-077667 A
Patent Literature 3: JP 2005-27515 A
Patent Literature 4: JP 2007-326814 A
Patent Literature 5: JP 2007-302610 A
Patent Literature 6: JP 08-291064 A

Non-Patent Literature

Non-Patent Literature 1: Shideng Bao et. al, Nature, 2006, doi: 10.1038/nature 05236

Non-Patent Literature 2: Heddleston J M. et. al., Cell Cycle, 2009, 8(20): 3274 to 3284

Non-Patent Literature 3: Justin D. Lathia et. al, PLoS One, 2011(6), e24807

Non-Patent Literature 4: Matsuoka H. et. al., Oncol. Rep.; 2000(7), 23 to 26

SUMMARY OF INVENTION

Problems to be Solved by the Invention

An object of the present invention is to provide a novel pharmaceutical for suppressing cancer stem cells.

Means for Solving the Problem

In view of such circumstances, in the present invention, a diligent research was conducted for seeking a novel pharmaceutical for suppressing cancer stem cells. As a result, it is found that a 2-nitroimidazole derivative, typically doranidazole and misonidazole, inhibits mitochondria in cancer stem cells and thus shows an effect of killing cancer stem cells, and the invention is thereby completed. Specifically, the present invention is as shown below.

[1] An inhibitor for inhibiting mitochondria in a cancer stem cell, comprising a 2-nitroimidazole derivative as an active ingredient.

[2] The inhibitor for inhibiting mitochondria according to [1], wherein the 2-nitroimidazole derivative is doranidazole, misonidazole, or etanidazole.

[3] An inducer for DNA double-strand break including a 2-nitroimidazole derivative as an active ingredient.

[4] A pharmaceutical for suppressing a cancer stem cell, comprising a 2-nitroimidazole derivative as an active ingredient.

[5] The pharmaceutical for suppressing a cancer stem cell according to [4], wherein the cancer stem cell is glioma, melanoma, or sarcoma.

[6] The pharmaceutical for suppressing a cancer stem cell according to [4] or [5], wherein the cancer stem cell is derived from metastatic cancer.

[7] The pharmaceutical for suppressing a cancer stem cell according to any of [4] to [6], wherein the pharmaceutical is used together with a cancer damaging means.

[8] The pharmaceutical for suppressing a cancer stem cell according to any of [4] to [7], wherein the cancer damaging means is administration of a cancer chemotherapeutic agent or of radiation.

[9] The pharmaceutical for suppressing a cancer stem cell according to [7] or [8], wherein the pharmaceutical is used in a pretreatment, concurrent treatment, or posttreatment of the cancer damaging means.

[10] A method for suppressing a cancer stem cell, the method including administering a 2-nitroimidazole derivative.

[11] A 2-nitroimidazole derivative for use in suppressing a cancer stem cell.

[12] Use of a 2-nitroimidazole derivative for producing a pharmaceutical for suppressing a cancer stem cell.

Advantageous Effects of the Invention

According to the present invention, a novel therapeutic means for cancer stem cells may be provided.

DETAILED DESCRIPTION OF THE INVENTION

The mitochondrial inhibitor, inducer for DNA double-strand break, and pharmaceutical for suppressing cancer stem cells of the present invention contain the 2-nitroimidazole derivative described above as an active ingredient. As a representative example of the 2-nitroimidazole derivative, for example, doranidazole, misonidazole, and etanidazole can be exemplified. Doranidazole can be produced in accordance with the method described in JP 3-223258 A or WO1994/014778. For example, the compound can be produced by condensing 2-nitro-1-trimethylsilylimidazole and 2-acetoxymethoxy-1,3,4-triacetoxybutane in the presence of Lewis acid, then reacting with, for example, sodium methoxide, and thus deacetylating. Misonidazole can be obtained by reacting 2-nitroimidazole and glydicidyl methyl ether by using sodium carbonate as a catalyst. Etanidazole can be obtained by reacting 2-nitroimidazole and bromomethyl ethyl acetate together with alkali substance such as sodium carbonate, to obtain 1-(2-ethoxycarbonyl)methyl-2-nitroimidazole, and then reacting the resultant with monoethanolamine. The compound thus obtained may be optionally purified by recrystallization or column chromatography, and can be used as, for example, a mitochondrial inhibitor.

Such a 2-nitroimidazole derivative inhibits energy metabolism of mitochondria in cancer stem cells. The inhibition involves inhibiting TCA cycle, specifically complex II of the mitochondria. This causes cancer stem cells to arrest the cell cycle in the G1 phase. In addition, the inhibition of mitochondria increases ROS, and thereby induces cell death. Since this cell death is suppressed by addition of ferrostatin, it may be identified to be ferroptosis. Cell death is not suppressed by a caspase inhibitor. This effect is observed in only cancer stem cells and no toxicity is exhibited in differentiated cancer cells under normoxic condition and hypoxic condition. It is therefore suggested that the 2-nitroimidazole derivative does not exhibit the above-described effect in differentiated cancer cells. Furthermore, the 2-nitroimidazole derivative similarly exhibits no toxicity to normal differentiated cells and stem cells. It is therefore suggested that the 2-nitroimidazole derivative does not exhibit this effect in these cells.

Furthermore, the 2-nitroimidazole derivative also induces double-strand break (DNA breakage effect) independently from the above-described effect under the condition of combined use with the administration of radiation. Radiosensitization effects are observed under hypoxic condition and normoxic condition, and double-strand break is markedly observed under hypoxic condition. Comparing to the phenomenon that, in differentiated cancer cells, the 2-nitroimidazole derivative exhibits almost no effect when radiation is not administered or is administered in normoxic conditions, and exhibits radiosensitization effects only when radiation is administered in hypoxic conditions it is found that the influence of the effect greatly differs between cancer stem cells and differentiated cancer cells. Furthermore, since this effect is not observed after cell differentiation, it may be considered that the effect also does not occur in normal cells. In other words, it can be said that the effect causes damage specifically in cancer stem cells. In particular, in a case where differentiated cancer cells are irradiated under hypoxic condition, although apoptosis is induced via partial damage such as hydroxylation of thymine in some cases, damage thereby is not enough for DNA breakage. Since DNA breakage is enhanced in cancer stem cells by radiation even under hypoxic condition, it can be said that the drug of the present invention is a very useful drug for cancer stem cell therapy.

As described above, the 2-nitroimidazole derivative of the present invention exhibits an excellent anti-cancer stem cell effect; however, the 2-nitroimidazole derivative exhibits almost no toxicity to differentiated cancer cells. Thus, in a case where the 2-nitroimidazole derivative is used in cancer therapy, it is preferable to use the derivative in combination with a damaging means for processing differentiated cancer cells. As the damaging means, radiation irradiation or administration of cancer chemotherapeutic agents such as a taxane agent, a platinum agent, and an alkylating agent are preferably exemplified. These damaging means can be used for treatment in accordance with the common cancer therapy guideline. The mitochondrial inhibitor of the present invention can be used for the damaging means in any of pretreatment, concurrent processing, and post treatment. A preferred aspect is one in which the mitochondrial inhibitor is used in all of pretreatment, concurrent processing, and post treatment. Since the mitochondrial inhibitor of the present invention exhibits no toxicity to normal cells, the mitochondrial inhibitor can also be administered during the interval period between using the damaging means for recovering physical fitness, and is preferably administered in such a period. This may be effective because cancer stem cells survive in cancer chemotherapy or radiation therapy, and it is therefore useful for the therapy to kill cancer stem cells prior to cancer chemotherapy or radiotherapy, or to kill cancer stem cells surviving after the above-described therapy. The 2-nitroimidazole derivative thus provides damage to and specifically inhibits mitochondria of cancer stem cells. Therefore, in a case where the 2-nitroimidazole derivative is used as a pharmaceutical for cancer stem cell treatment for the purpose of cancer therapy, it is preferably applied to cancers having many cancer stem cells. As an example of such a cancer, for example, melanoma, glioma, and sarcoma are preferably exemplified (reference literature; Non-Patent Literature 3 and Elsa Quintana et. al, Nature. 2008 Dec. 4; 456(7222): 593 to 598). Furthermore, since cancer stem cells play an important roll in metastasis of cancer, the 2-nitroimidazole derivative is also preferably used for the purpose of preventing the cancer which is generated due to metastasis or the metastasis of metastatic cancer.

Thus, the 2-nitroimidazole derivative leads cancer stem cells to cell death, shows an excellent effect of suppressing growth of cancer stem cells, and is therefore useful as a pharmaceutical for cancer stem cells. In the 2-nitroimidazole derivative, in a case where doranidazole or etanidazole is used as a pharmaceutical for suppressing cancer stem cells, it is preferred to administer 0.5 to 10 g of doranidazole or etanidazole per day orally or by injection (including continuous infusion). This is because doranidazole and etanidazole show only an effect as a hypoxic cell radiosensitizer on differentiated cancer cells other than cancer stem cells. The toxicity of doranidazole and etanidazole is very low, LD50 is 5 g/Kg or more. Since the LD50 of misonidazole is about 1 g/kg, the dose of the misonidazole may be determined to be about ⅕ of doranidazole or etanidazole.

Such a compound can be processed into pharmaceutical formulations together with optional ingredients normally used for formulation, and used. For summarizing the above description, a table for comparing cancer stem cells and differentiated cancer cells is shown below.

TABLE 1

| | Cancer stem cell | | Differentiated cancer cell | |
|---|---|---|---|---|
| Item | Hypoxic condition | Normoxic condition | Hypoxic condition | Normoxic condition |
| Metabolism | Normal (no significant decrease) | Normal | Metabolism decreases | Normal |
| Effect of 2-nitroimidazole | | | | |
| Mitochondria | Inhibited | Inhibited | No report of inhibition | No report of inhibition |
| TCA cycle | Complex II inhibited | Complex II inhibited | No report of effect | No report of effect |
| Cell cycle | Terminated in G1 | Terminated in G1 | No report of effect | No report of effect |
| Cell death | Ferroptosis | Ferroptosis | Not induced cell death | Not induced cell death |
| Combined use with radiation | Ferroptosis + DSB | Ferroptosis + DSB | Thymine hydroxylation + apoptosis | Considered to be DSB, but no detailed report |

EXAMPLES

Hereinafter, the present invention will be further described in detail with reference to Examples.

Example 1

Figure 1:
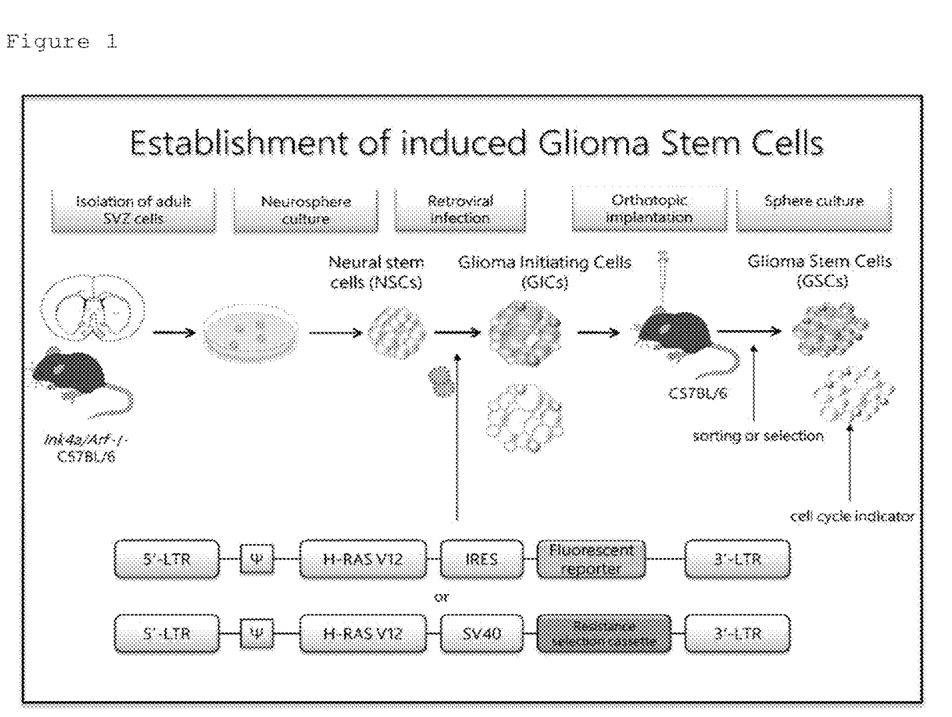
FIG. 1 is a drawing illustrating a method of preparing cells for use in in vitro assay.

In accordance with the literature (Sampetrean O. et. al., Neoplasia, 13(9) 2011, 784 to 791), the subventricular zone was resected from Ink4a/Arf deficient mice and subjected to trypsin treatment to obtain spheroid-forming cells. The resulting spheroids were cultured in a culture medium containing no differentiation-inducing component (DMEM/F12 in which 20 ng/mL of EGF, 20 ng/mL of FGF, B27 supplement in which vitamin A was removed, 200 ng/mL of heparan sulfate, 100 U/mL of penicillin, and 100 U/mL of streptomycin were added) in a flow of 5% carbon dioxide at 37° C. Then, a constitutively active, mutated form of H-Ras and, as necessary, reporter cassettes for detecting, for example, fluorescent signals or selection marker for cell selection, for example, drug-resistant cassettes, were incorporated into cancer stem cells for transformation, and cultured to obtain spheroid-forming cells. These cells were transplanted to the brains of C57BL/6 mice, then the formed brain tumors were resected and subjected to trypsin treatment to obtain cells. Drug-resistant or fluorescent reporter-positive cells were sorted, and then cell cycle markers were introduced into part of the cells. Thus-obtained spheroid-forming cells were cultured under the above-described culturing condition, and used as a sample. The outline is shown in FIG. 1.

Figure 2:
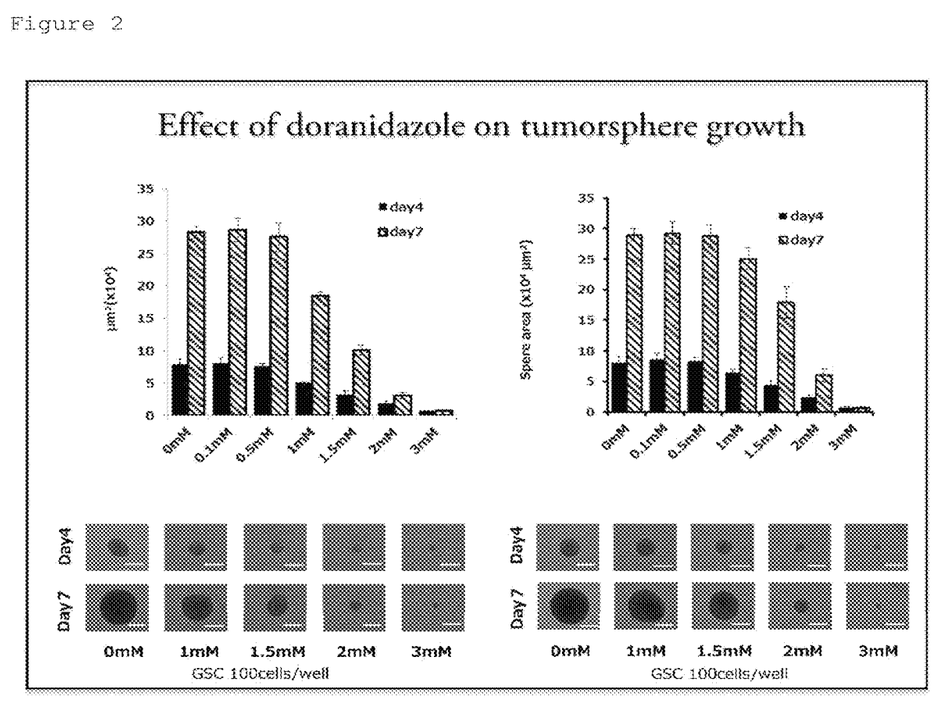
FIG. 2 is a drawing illustrating the result of in vitro assay.

The above-described cells were cultured in a 96-well plate in the above-described culture mediums to which various concentration of analytes were added. The results are shown in FIG. 2. It is found that addition of doranidazole suppresses the growth of spheroids which is characteristics of stem cells.

Figure 3:
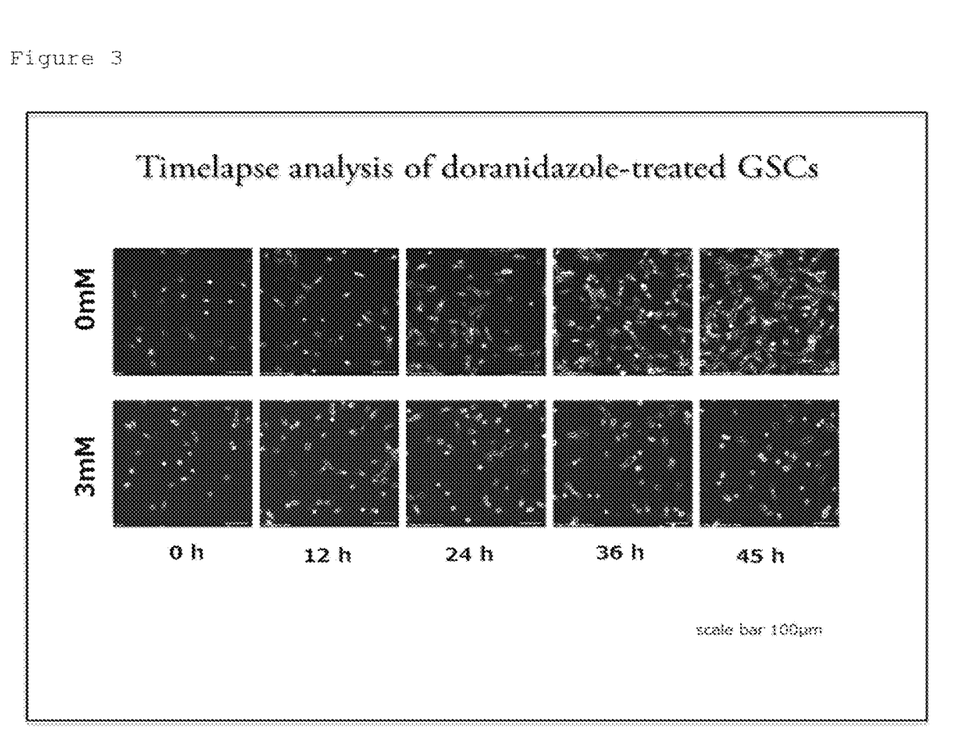
FIG. 3 is a drawing illustrating the result of in vitro assay.

The above cells were subjected to monolayer culture. Then, various concentrations of analyte were added thereto and cultured in the above-described culture mediums. The results are shown in FIG. 3. It is found that addition of doranidazole arrests the cell cycle in the G1 phase and suppresses growth.

Figure 4:
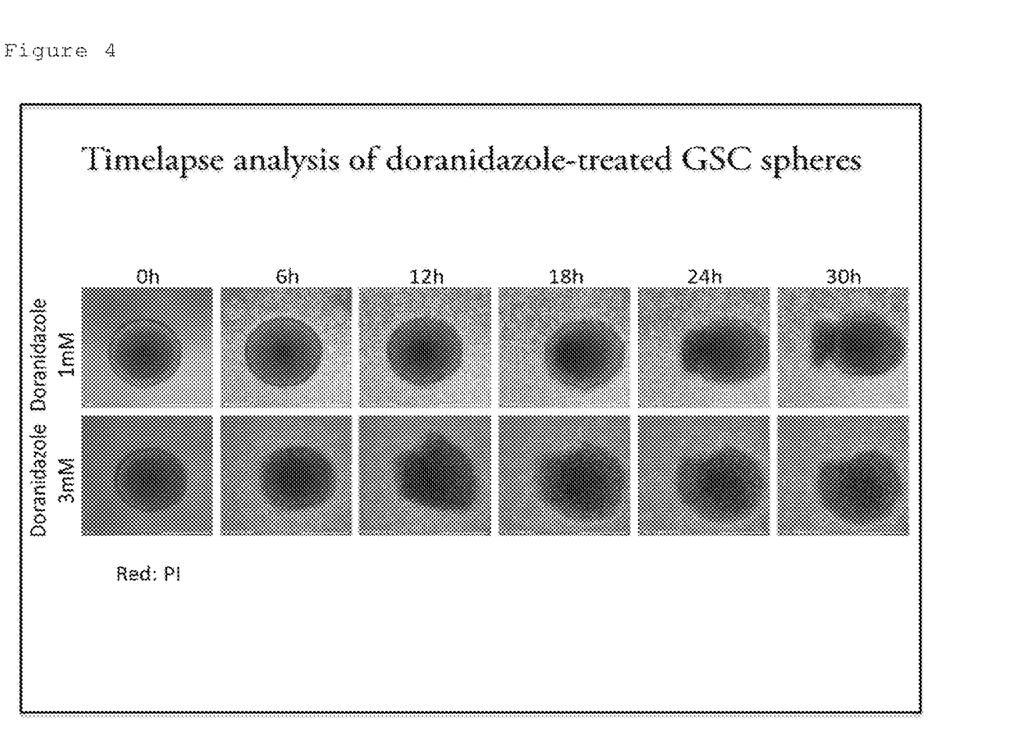
FIG. 4 is a drawing illustrating the cell death in Example 1.
Figure 5:
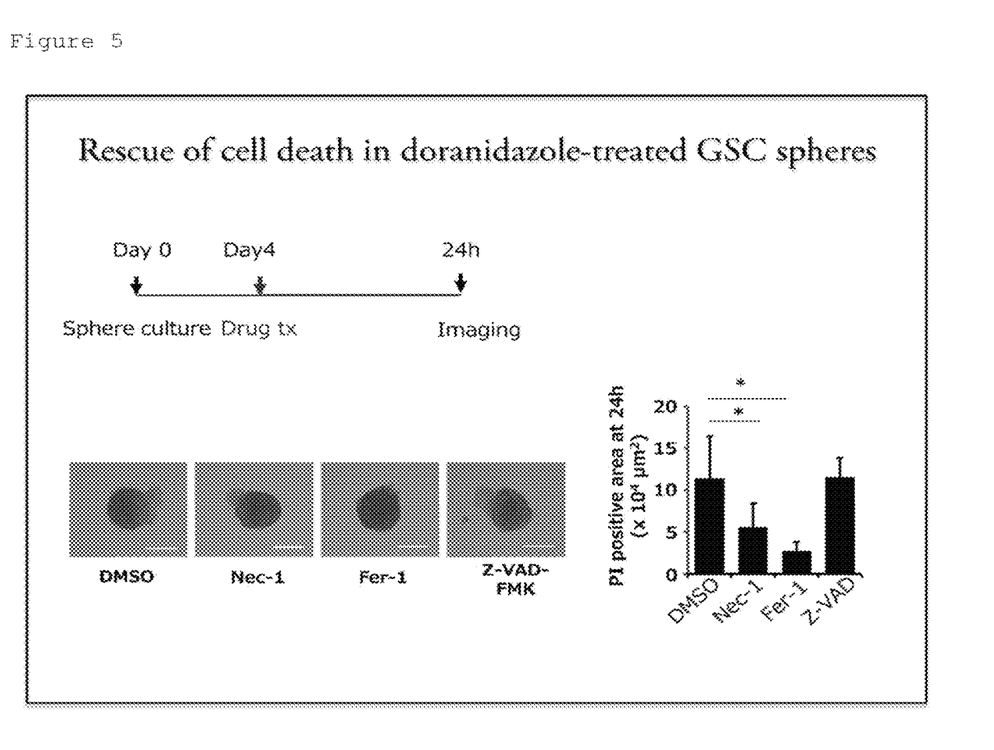
FIG. 5 is a drawing illustrating the result of studying the state of cell death in Example 1.

Furthermore, FIG. 4 shows the result when we focus on one spheroid to which doranidazole and propidium iodide (PI) were added, and monitored the state of the spheroid overtime. It is found that a PI positive area increases with the lapse of time and cell death is induced. In addition, it is found that cell death is induced by doranidazole in dose dependent manner. This cell death is significantly suppressed by addition of ferrostatin 1 compared to addition of DMSO (solvent control), necrostatin 1 which is a necroptosis inhibitor, and Z-VAD-FMK which is a caspase (apoptosis) inhibitor as shown in FIG. 5. Thus, it is found that this cell death is ferroptosis (reference literature; Y Xie et. al, Cell Death and Differentiation, (2016) 23, 369 to 379).

This cell death was similarly studied by using misonidazole, and the cell death was similarly confirmed. As for metronidazole which is a 5-nitroimidazole derivative, no cell death was observed. Thus, it is found that the cell death is a phenomenon specific to a 2-nitroimidazole derivative.

Example 2

Figure 6:
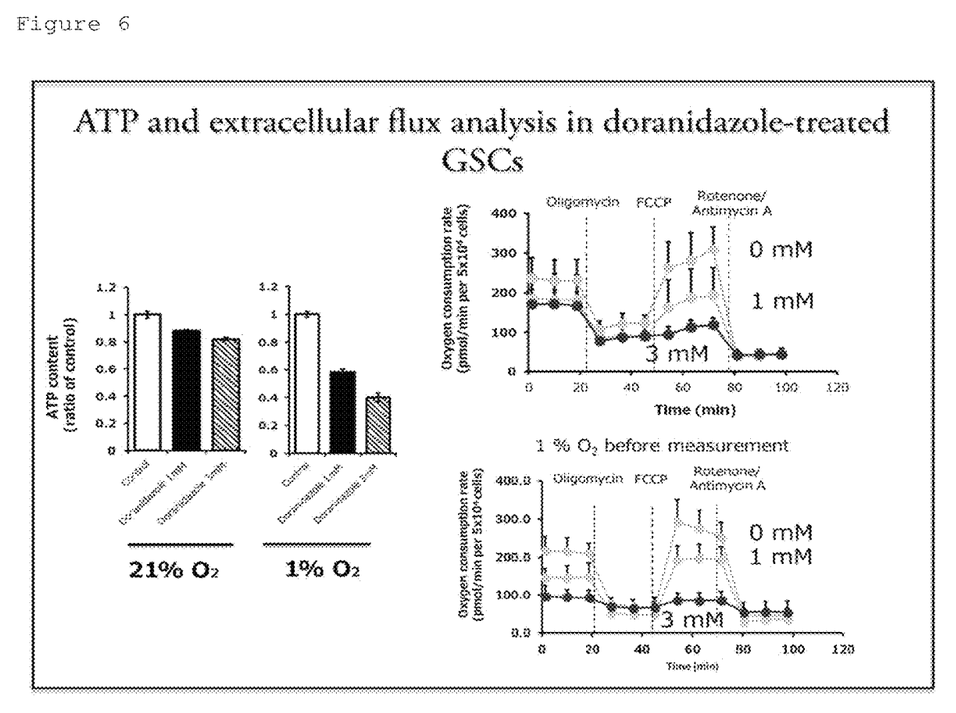
FIG. 6 is a drawing illustrating the result of Example 2.

Since the cell cycle was arrested in the G1 phase, a decrease in energy metabolism was suspected. ATP levels under 21% oxygen (normoxic condition) and 1% oxygen (hypoxic condition) were measured using the same cells as in Example 1. The results are shown in FIG. 6. It shows that ATP content of cancer stem cells was decreased by administration of doranidazole. From this, suppression of mitochondrial function was suspected, and so, mitochondrial function was evaluated by extracellular flux analysis. The results are shown in FIG. 6. It shows that, in cells cultured under 21% oxygen (normoxic condition) and 1% oxygen (hypoxic condition), oxygen consumption and reserve capacity of mitochondria were decreased depending on the concentration of doranidazole.

Example 3

Figure 7:
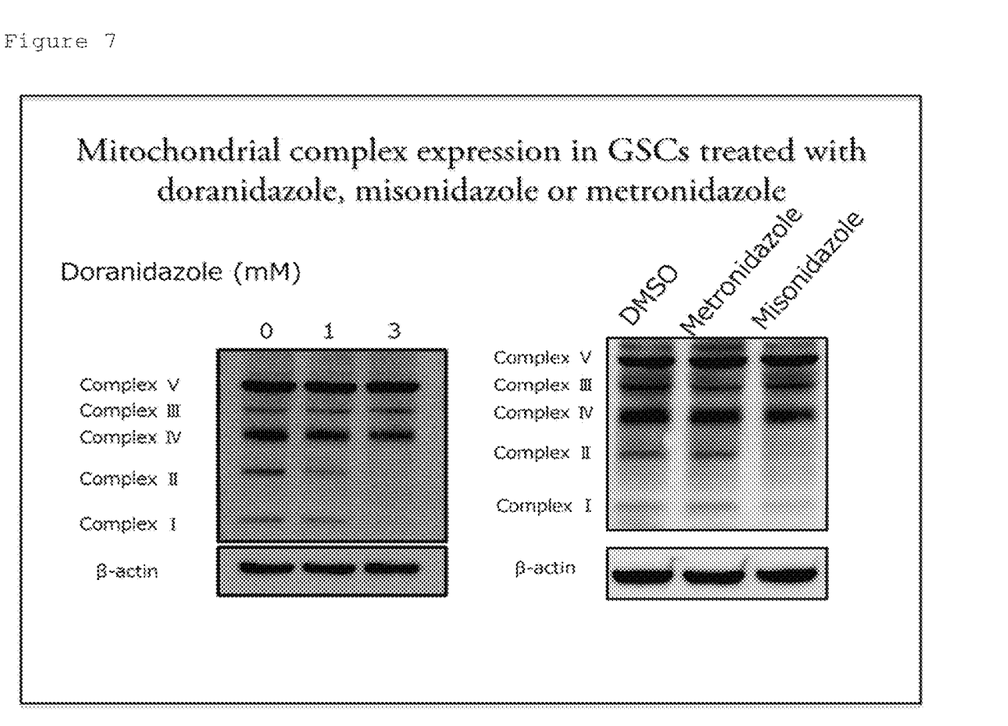
FIG. 7 is a drawing illustrating the result of Example 3.

Furthermore, protein was extracted from cells of Example 1, and the expression levels of mitochondrial complex I to V were measured by electrophoresis and Western Blot. The results are shown in FIG. 7. It shows that the expression of complex II was remarkably decreased by administration of doranidazole and misonidazole.

Example 4

Figure 8:
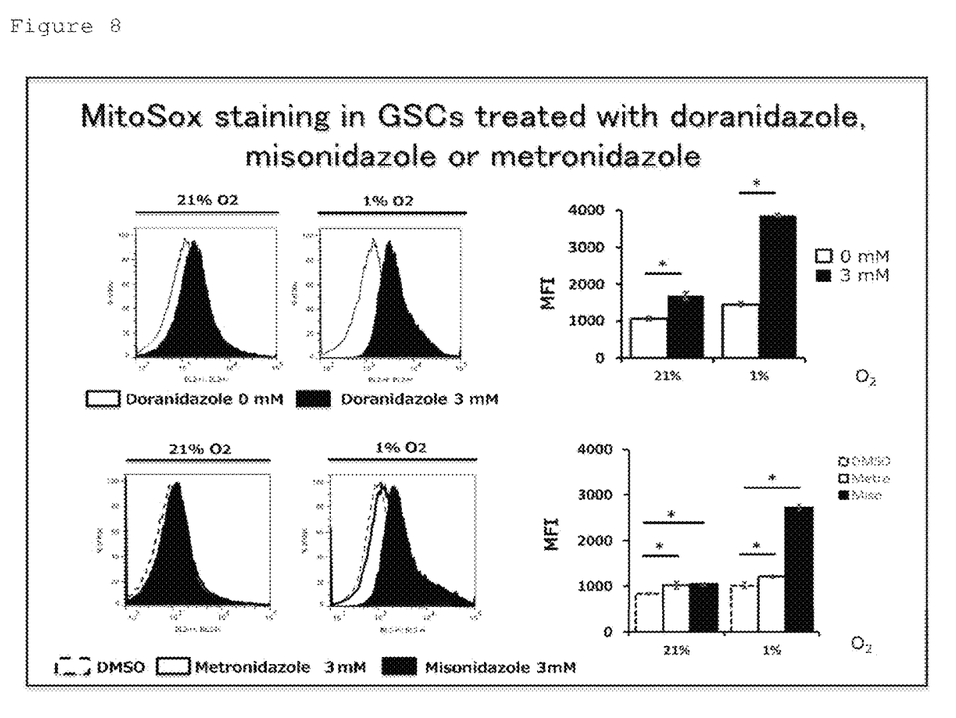
FIG. 8 is a drawing illustrating the result of Example 4.

Using Mito Sox staining, reactive oxygen species (ROS) in mitochondria was quantified by flow cytometry for the cells cultured according to Example 1, with or without doranidazole, misonidazole, or metronidazole. The results are shown in FIG. 8. It shows that ROS significantly increases in the presence of doranidazole and misonidazole. In other words, the processing of generated ROS is inhibited by the 2-nitroimidazole derivative, resulting in ROS increase. Such a phenomenon is not observed when using a 5-nitroimidazole derivative metronidazole.

Example 5

Using the method similar to Example 1, the degree of induction of differentiation was altered by changing the culture mediums, to observe the effect thereby.

Figure 9:
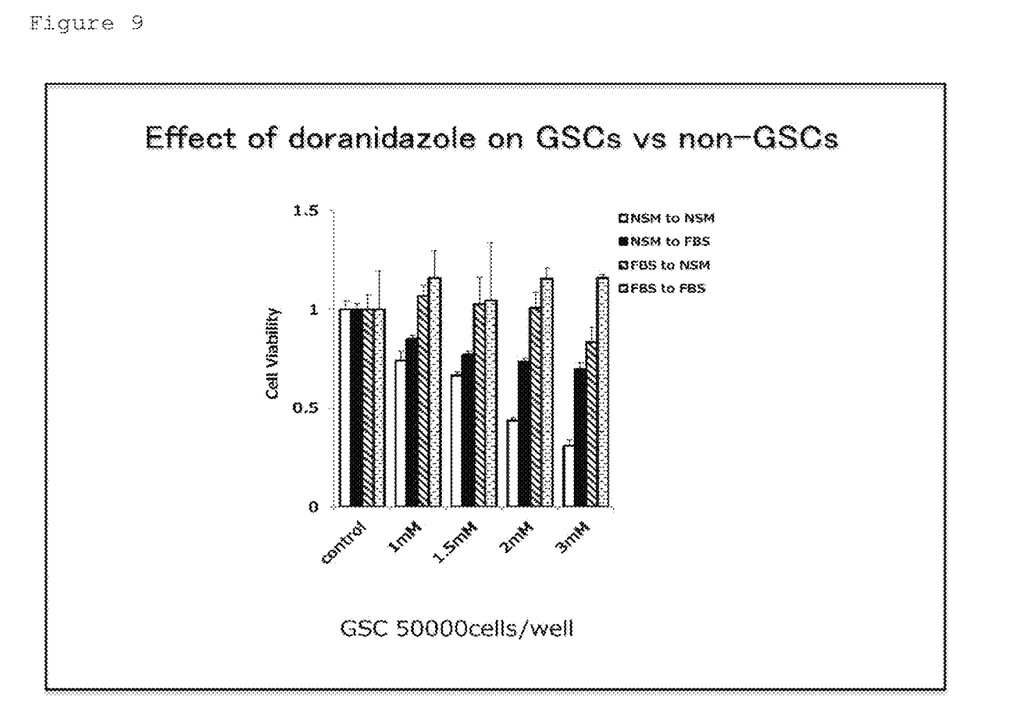
FIG. 9 is a drawing illustrating the result of Example 5.

Specifically, a group cultured in a serum-free culture medium of Example 1 for consecutive 4 days; a group cultured in a serum-free culture medium for 3 days, and then cultured in a serum-containing culture medium for 1 day; a group cultured in a serum-containing culture medium for 3 days, and then cultured in a serum-free culture medium for 1 day; and the remaining one group cultured in a serum-containing culture medium for 4 days; were prepared. According to such culturing, the degree of induction of differentiation by serum was altered and the effect of doranidazole was confirmed. The results are shown in FIG. 9. It shows that when the degree of induction of differentiation by serum is low, the effect of doranidazole is remarkable. In other words, it shows that doranidazole significantly exhibits specific effects to undifferentiated cancer stem cells.

Example 6

Figure 10:
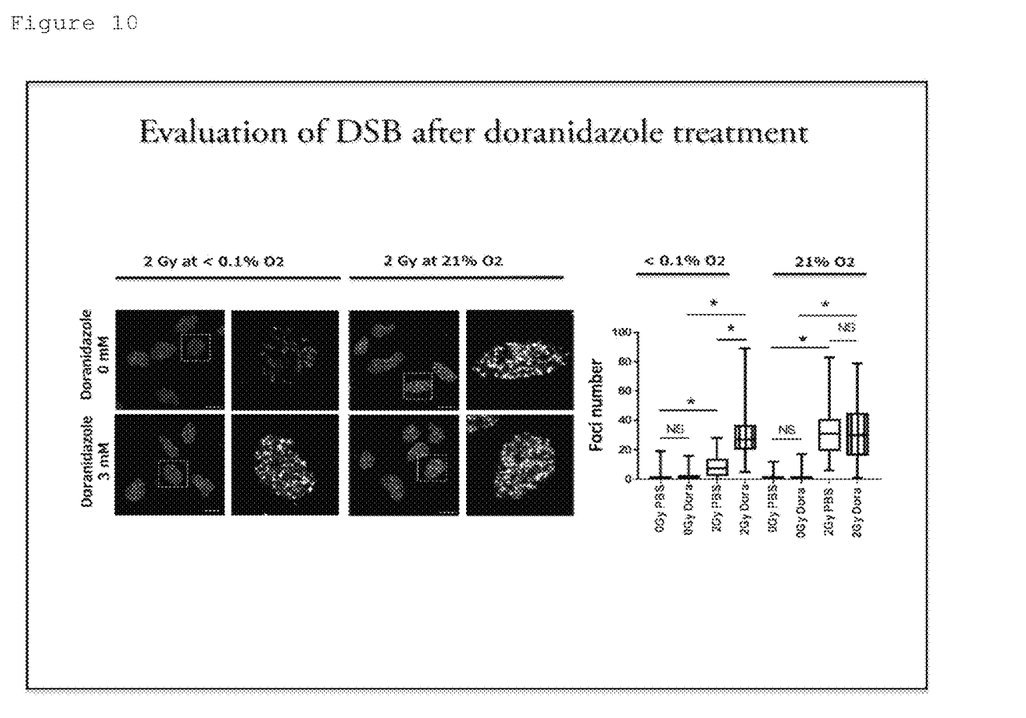
FIG. 10 is a drawing illustrating the result of Example 6.

Cells cultured according to the method of Example 1, with or without doranidazole, were irradiated, followed by double staining with Hoechst 33324 and γH2AX, and then double-strand break was quantified. The results are shown in FIG. 10. This shows that doranidazole, under hypoxic condition, significantly enhances radiation-induced double-strand break in cancer stem cells.

INDUSTRIAL APPLICABILITY

The present invention can be applied to pharmaceuticals for therapy of cancers containing cancer stem cells.

The invention claimed is:
1. A method for suppressing a cancer stem cell, the method comprising:
   contacting the cancer stem cell with a pharmaceutical comprising a 2-nitroimidazole derivative as an active ingredient,
   wherein the cancer stem cell is glioma, melanoma, or sarcoma, and
   wherein the 2-nitroimidazole derivative is doranidazole, misonidazole, or etanidazole.
2. The method according to claim 1, wherein the cancer stem cell is derived from metastatic cancer.
3. The method according to claim 1, wherein the pharmaceutical is contacted together with a cancer damaging means.
4. The method according to claim 3, wherein the cancer damaging means is administration of a cancer chemotherapeutic agent or radiation.

5. The method according to claim 3, wherein the pharmaceutical is suitable for pretreatment, concurrent treatment, or posttreatment of the cancer damaging means.

6. A method for suppressing growth of a cancer stem cell, the method comprising:
   administering a 2-nitroimidazole derivative to a subject in need thereof,
   wherein the cancer stem cell is glioma, melanoma, or sarcoma, and
   wherein the 2-nitroimidazole derivative is doranidazole, misonidazole, or etanidazole.

* * * * *